United States Patent [19]

Cullen et al.

[11] 4,344,946

[45] Aug. 17, 1982

[54] 2,6-DIAMINO-BENZO[1,2-d:5,4-d']BIS-THIAZOLES AND SALTS THEREOF

[75] Inventors: Ernest Cullen, Montreal, Canada; Genus Possanza, Ridgefield; Patrick B. Stewart, Washington Depot, both of Conn.

[73] Assignee: Boehringer Ingelheim GmbH, Ingelheim am Rhein, Fed. Rep. of Germany

[21] Appl. No.: 182,077

[22] Filed: Aug. 28, 1980

Related U.S. Application Data

[63] Continuation of Ser. No. 928,827, Jul. 28, 1978, abandoned.

[30] Foreign Application Priority Data

Aug. 13, 1977 [DE] Fed. Rep. of Germany ....... 2736652

[51] Int. Cl.³ .................. A61K 31/495; C07D 521/00
[52] U.S. Cl. .................................... 424/250; 424/267;
424/270; 544/54; 544/58.7; 544/80; 544/133;
544/135; 544/357; 544/358; 544/360; 546/187;
548/151
[58] Field of Search .................. 548/151; 544/54, 58.7,
544/133, 357, 80, 135, 360, 358; 546/187;
424/250, 267, 270

[56] References Cited

U.S. PATENT DOCUMENTS

| 2,140,540 | 12/1938 | Middleton et al. | 548/151 |
| 2,182,815 | 12/1939 | Middleton et al. | 548/151 |
| 3,489,558 | 1/1970 | Clecak et al. | 548/151 |
| 3,501,293 | 3/1970 | Clecak et al. | 548/151 |
| 4,065,462 | 12/1977 | Frey et al. | 548/151 |

FOREIGN PATENT DOCUMENTS 675033 11/1964 Italy ................................... 548/151

Primary Examiner—Anton H. Sutto
Assistant Examiner—James H. Turnipseed
Attorney, Agent, or Firm—Hammond & Littell, Weissenberger & Muserlian

[57] ABSTRACT

Compounds of the formula

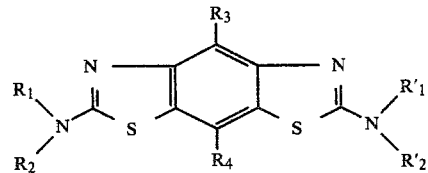

wherein
$R_1$ and $R_1'$, which may be identical to or different from each other, are each hydrogen or alkyl of 1 to 2 carbon atoms;
$R_2$ and $R_2'$, which may be identical to or different from each other, are each hydrogen or

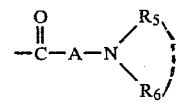

but other than both hydrogen at the same time, where
A is alkylene of 1 to 2 carbon atoms,
$R_5$ is hydrogen, lower alkyl, lower alkylamino-lower alkyl, lower alkoxy-lower alkyl, hydroxycarbonyl-lower alkyl, cycloalkyl of 5 to 8 carbon atoms, lower alkyl-cycloalkyl of 5 to 8 carbon atoms, phenyl or morpholino;
$R_6$ is hydrogen, lower alkyl, lower alkylamino-lower alkyl or lower alkoxy-lower alkyl; or
$R_5$ and $R_6$, together with each other and the nitrogen atom to which they are attached, form a 5-, 6- or 7-membered heterocyclic ring, where a 5- or 6-membered ring may comprise an additional sulfur or nitrogen heteroatom, and in the latter case said heterocyclic ring may optionally have one or two lower alkyl substituents, a lower alkoxy-carbonyl, a lower alkoxy-carbonyl-methyl, a hydroxy-lower alkyl, a trifluoroethyl, a cycloalkyl, a lower alkyl-cycloalkyl, a cyclohexylmethyl, a benzyl, a pyridyl, a piperidino, a phenyl, a fluoro-phenyl, a chloro-phenyl, a trifluoromethyl-phenyl, or an acetyl-phenyl substituent attached thereto; and
$R_3$ and $R_4$, which may be identical to or different from each other, are each hydrogen, chlorine, bromine, lower alkyl, lower alkoxy, lower alkanoyl, hydroxycarbonyl, lower alkoxy-carbonyl, aminocarbonyl, phenyl, trifluoromethyl, nitro, cyano or amino;

and non-toxic, pharmacologically acceptable acid addition salts thereof. The compounds as well as the salts are useful as antiarthritics and antirheumatics.

20 Claims, No Drawings

2,6-DIAMINO-BENZO[1,2-d:5,4-d']BIS-THIAZOLES AND SALTS THEREOF

This is a continuation of Ser. No. 928,827, filed July 28, 1978, now abandoned.

This invention relates to novel 2,6-diamino-benzo-[1,2-d:5,4-d']bisthiazoles and acid addition salts thereof, as well as to methods of preparing these compounds, pharmaceutical compositions containing them as active ingredients, and methods of using them as antiarthritics and antirheumatics.

More particularly, the present invention relates to a novel class of compounds represented by the formula

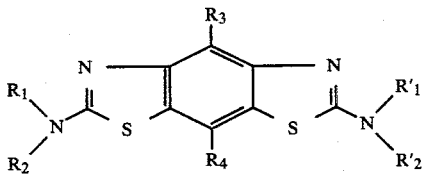
(I)

wherein
$R_1$ and $R_1'$, which may be identical to or different from each other, are each hydrogen or alkyl of 1 to 2 carbon atoms;
$R_2$ and $R_2'$, which may be identical to or different from each other, are each hydrogen or

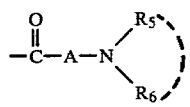

but other than both hydrogen at the same time, where
A is alkylene of 1 to 2 carbon atoms,
$R_5$ is hydrogen, lower alkyl, lower alkylamino-lower alkyl, lower alkoxy-lower alkyl, hydroxycarbonyl-lower alkyl, cycloalkyl of 5 to 8 carbon atoms, lower alkyl-cycloalkyl of 5 to 8 carbon atoms, phenyl or morpholino;
$R_6$ is hydrogen, lower alkyl, lower alkylamino-lower alkyl or lower alkoxy-lower alkyl; or
$R_5$ and $R_6$, together with each other and the nitrogen atom to which they are attached, form a 5-, 6- or 7-membered heterocyclic ring, where a 5- or 6- membered ring may comprise an additional sulfur or nitrogen heteroatom, and in the latter case said heterocyclic ring may optionally have one or two lower alkyl substituents, a lower alkoxy-carbonyl, a lower alkoxy-carbonyl-methyl, a hydroxy-lower alkyl, a trifluoroethyl, a cycloalkyl, a lower alkylcycloalkyl, a cyclohexylmethyl, a benzyl, a pyridyl, a piperidino, a phenyl, a fluoro-phenyl, a chloro-phenyl, a trifluoromethyl-phenyl or an acetyl-phenyl substituent attached thereto; and
$R_3$ and $R_4$, which may be identical to or different from each other, are each hydrogen, chlorine, bromine, lower alkyl, lower alkoxy, lower alkanoyl, hydroxycarbonyl, lower alkoxy-carbonyl, aminocarbonyl, phenyl, trifluoromethyl, nitro, cyano or amino;
and non-toxic, pharmacologically acceptable acid addition salts thereof.

The terms "lower alkyl" and "lower alkoxy" as used herein are intended to designate alkyl and alkoxy of 1 to about 6 carbon atoms, and those of 1 to 3 carbon atoms are preferred. Specific examples are methyl, ethyl, propyl, isopropyl, methoxy, ethoxy and propoxy. Likewise, the term "lower alkanoyl" is intended to designate alkanoyl of 1 to 6 carbon atoms, preferably of 2 to 3 carbon atoms, such as acetyl or propionyl.

A preferred sub-genus under the genus defined by formula I is constituted by those compounds where
$R_1$ and $R_1'$ are hydrogen;
$R_2$ and $R_2'$ are both $-CO-CH_2-NR_5R_6$;
where $R_5$ and $R_6$ are each methyl, ethyl or, together with each other and the nitrogen atom to which they are attached, piperidino or piperazino, where the heterocycles may optionally have a methyl, piperidino, phenyl or trifluoromethyl-phenyl substituent attached thereto; and
$R_3$ and $R_4$, which may be identical to or different from each other, are each hydrogen, chlorine, bromine, methyl, methoxy, cyano or trifluoromethyl;
and non-toxic, pharmacologically acceptable acid addition salts thereof.

An especially preferred sub-genus is constituted by those compounds of the formula I where
$R_1$ and $R_1'$ are both hydrogen;
$R_2$ and $R_2'$ are both $-CO-CH_2-NR_5R_6$,
where $R_5$ and $R_6$ are ethyl or, together with each other and the nitrogen atom to which they are attached, piperidino, methyl-piperdino, piperazino or methyl-piperazino;
$R_3$ is hydrogen, methyl-piperazino, chlorine or bromine; and
$R_4$ is hydrogen, chlorine, bromine, cyano or trifluoromethyl;
and non-toxic, pharmacologically acceptable acid addition salts thereof.

The compounds embraced by formula I may be prepared by the following methods:

METHOD A

By reacting a compound of the formula

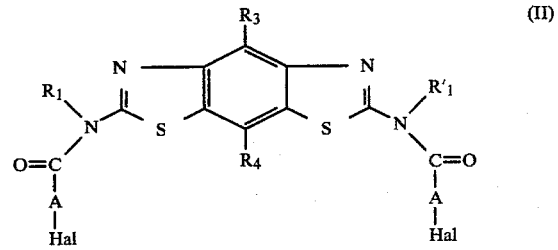
(II)

wherein
$R_1$, $R_1'$, $R_3$, $R_4$ and A have the same meanings as in formula I, and
Hal is halogen,
with an amine of the formula

(III)

wherein $R_5$ and $R_6$ have the same meanings as in formula I.

The reaction is advantageously performed in an inert solvent, such as a lower alkanol, dioxane, dimethylformamide, acetonitrile, dimethylsulfoxide, tetrahydrofuran, ethyl acetate, chloroform, dichloroethane, methyl isobutyl ketone, methylene chloride, benzene, toluene or xylene. In those instances where the amine reactant of the formula III is a liquid, the reaction may also be carried out without a solvent. The reaction temperature is preferably between 60° C. and the reflux temperature of the reaction mixture.

METHOD B

By reacting a 2,6-diamino-benzo[1,2-d:5,4-d']bisthiazole of the formula

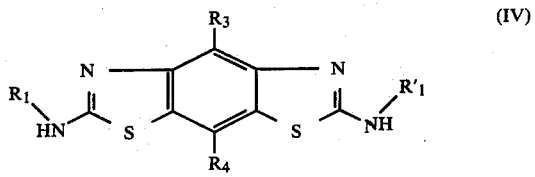

wherein $R_1$, $R_1'$, $R_3$ and $R_4$ have the same meanings as in formula I, with an aminoalkyl-carboxylic acid of the formula

wherein $R_5$, $R_6$ and A have the same meanings as in formula I or a reactive deviative thereof, such as the methyl, ethyl, or phenyl ester, in an inert solvent.

If the free carboxylic acid is used, the reaction is advantageously carried out in the presence of an activating agent such as a carbodiimide, for instance 3-ethyl-3-(3-dimethylamino-propyl)-carbodiimide; if the methyl or ethyl ester is used, the presence of metallic sodium or lithium, sodium hydride, sodium methylate, sodium ethylate or lithium diethylamide is required.

If the reactant of the formula III is the free carboxylic acid, the inert solvent can be ether, tetrahydrofuran, methylene chloride or acetonitrile. If the reactant of the formula III is a reactive derivative, the inert solvent is preferably a lower alkanol such as methanol or ethanol, toluene, dioxane, tetrahydrofuran, dimethylformamide or dimethylsulfoxide.

The reaction temperature may vary between room temperature and the reflux temperature of the reaction mixture, depending upon the particular starting materials which are used and the reaction conditions which are applied.

The reactions described under methods A and B yield in most cases not only the bis-aminoacylamino compound, that is, where $R_2$ and $R_2'$ in formula I are both —CO—A—$NR_5R_6$ as defined above, but also varying amounts of the corresponding mono-aminoacylamino compound, that is, where only one of $R_2$ and $R_2'$ is —CO—A—$NR_5R_6$ and the other is hydrogen. The ratio of these two types of compounds in the reaction product can be controlled within certain limits; for instance, we have found that when a solvent such as dioxane or dimethylsulfoxide is used, the bis-aminoacylamino compounds are predominantly formed, whereas when dimethylformamide or ethanol is used as the solvent, good yields of both the bis- and the monoaminoacylamino compounds are obtained.

METHOD C

For the preparation of a compound of the formula I wherein $R_3$ and/or $R_4$ are chlorine, bromine or nitro, by introducing one or two chlorine or bromine atoms or one or two nitro-substituents into a 4- and/or 8- unsubstituted compound of the formula I, i.e. where $R_3$ and/or $R_4$ are hydrogen.

The introduction of chlorine or bromine atoms may be effected by conventional halogenation methods, for instance with elemental chlorine or bromine, or with N-bromo-or N-chloro-succinimide, where the particular reaction conditions depend primarily upon the halogenating agent which is used. Thus, for example, the chlorination with elemental chlorine may be effected with chloroform/pyridine as the solvent medium at room temperature. The bromination with elemental bromine may be performed in the same solvent medium, but at higher temperatures. Triethyl phosphate has proved to be particularly well suited as the solvent medium.

The introduction of nitro-substituents may also be effected by conventional methods, such as with nitric acid or with an alkali metal nitrate in the presence of sulfuric acid, preferably at low temperatures between about −10° and +10° C.

The compounds embraced by formula I are organic bases and therefore form addition salts with inorganic or organic acids. Examples of non-toxic, pharmacologically acceptable acid addition salts are those formed with hydrohalic acids, especially hydrochloric or hydrobromic acid, nitric acid, sulfuric acid, o-phosphoric acid, tartaric acid, citric acid, maleic acid, fumaric acid, propionic acid, butyric acid, acetic acid, succinic acid, methanesulfonic acid, benzenesulfonic acid, p-toluenesulfonic acid, 8-chlorotheophylline or the like.

The following are examples of compounds of the formula I which may be prepared by methods A to C above:

2,6-Bis-(diethylamino-acetylamino)-benzo[1,2-d:5,4-d']bisthiazole,
2,6-bis[N'-methyl-N'-(N,N-diethylamino-acetyl)-amino]benzobisthiazole,
2,6-bis-(piperidino-acetylamino)-benzo[1,2-d:5,4-d']bisthiazole,
2,6-bis[(N-methyl-N-cyclohexylamino)acetylamino]-benzo-[1,2-d:5,4-d']bisthiazole,
2,6-bis-(diethylamino-acetylamino)-4-chloro-8-trifluoromethylbenzo[1,2-d:5,4-d']bisthiazole,
2,6-bis-(diethylamino-acetylamino)-4-chloro-8-cyano-benzo[1,2-d:5,4-d']bisthiazole,
2,6-bis-(diethylamino-acetylamino)-4-methyl-benzo[1,2-d:5,4-d']bisthiazole,
2,6-Bis-(dimethylamino-acetylamino)-benzo[1,2-d:5,4-d']-bisthiazole,
2,6-bis-(ethylamino-acetylamino)-benzo[1,2-d:5,4-d']-bisthiazole,
2,6-bis-(diethylamino-acetylamino)-4,8-dichloro-benzo[1,2-d:5,4-d']bisthiazole,
2,6-bis(di-n-propylamino-acetylamino)-benzo[1,2-d:5,4-d']-bisthiazole,
2,6-bis-(N-carbethoxypiperazino-acetylamino)-benzo-[1,2-d:5,4-d']bisthiazole,
2,6-bis[N-(β-hydroxyethyl)-piperazino-acetylamino]-benzo-[1,2-d:5,4-d']bisthiazole, 2,6-bis-(3-methylpiperidino-acetylamino)-benzo[1,2-d:5,4-d']-bisthiazole,
2,6-bis-(2-ethylpiperidino-acetylamino)-benzo[1,2-d:5,4-d']-bisthiazole,
2,6-bis-[1-(p-fluorophenyl)-piperazino-acetylamino]-benzo-[1,2-d:5;4-d']bisthiazole,
2,6-bis-(4-methylpiperidino-acetylamino)-benzo[1,2-d:5,4-d']bisthiazole,
2,6-bis-(4-methylpiperazino-acetylamino)-benzo[1,2-d:5,4-d']bisthiazole,
2,6-bis-(di-isopropylamino-acetylamino)-benzo[1,2-d:5,4-d']bisthiazole,
2,6-bis-(anilino-acetylamino)-benzo[1,2-d:5,4-d']bisthiazole,
2,6-bis-(diethylamino-acetylamino)-4-chloro-8-methoxy-benzo[1,2-d:5,4-d']bisthiazole,
2,6-bis-(diethylamino-acetylamino)-4-acetyl-8-phenyl-benzo[1,2-d:5,4-d']bisthiazole,
2,6-bis-(di-n-propylamino-acetylamino)-4-trifluoromethyl-8-aminocarbonyl-benzo[1,2-d:5,4-d']bisthiazole,
2,6-bis-(diethylamino-propionylamino)-benzo[1,2-d:5,4-d']bisthiazole,
2,6-bis-(piperidino-piperidino-acetylamino)-benzo[1,2-d:5,4-d']bisthiazole,
2,6-bis-(4-phenylpiperidino-acetylamino)-benzo[1,2-d:5,4-d']bisthiazole
2,6-bis-[di-(ethoxyethyl)-amino-acetylamino]benzo[1,2-d:5,4-d']bisthiazole,
2,6-bis-(N-ethyl-N-hydroxycarbonylmethylamino-acetylamino)benzo[1,2-d:5,4-d']bisthiazole,
2,6-bis-(thiomorpholino-acetylamino)-benzo[1,2-d:5,4-d']bisthiazole,
2,6-bis-(piperazino-acetylamino)-benzo[1,2-d:5,4-d']bisthiazole,
2,6-bis-(cyclopentylamino-acetylamino)-benzo[1,2-d:5,4-d']bisthiazole,
2,6-bis-(N-methyl-N-cycloheptylamino-acetylamino)-benzo[1,2-d:5,4-d']bisthiazole,
2,6-bis-(diethylamino-acetylamino)-4-bromo-benzo-[1,2-d:5,4-d']bisthiazole,
2,6-bis-(pyrrolidino-acetylamino)-benzo[1,2-d:5,4-d']bisthiazole,
2,6-bis-(hexamethyleneimino-acetylamino)-benzo[1,2-d:5,4-d']bisthiazole,
2,6-bis[1-(p-chlorophenyl)-piperazino-acetylamino]benzo[1,2-d:5,4-d']bisthiazole,
2,6-bis-(thiazolino-acetylamino)-benzo[1,2-d:5,4-d']bisthiazole,
2-amino-6(diethylamino-acetylamino)-benzo[1,2-d:5,4-d']bisthiazole,
2-amino-6-(di-n-propylamino-acetylamino)-benzo[1,2-d:5,4-d']bisthiazole,
2-amino-6-(carbethoxypiperazino-acetylamino)-benzo[1,2-d:5,4-d']bisthiazole,
2-amino-6-(3-methylpiperidino-acetylamino)-benzo[1,2-d:5,4-d']bisthiazole,
2-amino-6-(2-ethylpiperidino-acetylamino)-benzo-[1,2-d:5,4-d']bisthiazole,
2-amino-6[1-(p-fluorophenyl)-piperazino-acetylamino]-benzo[1,2-d:5,4-d']bisthiazole,
2-amino-6-(4-methylpiperidino-acetylamino)-benzo[1,2-d:5,4-d']bisthiazole,
2,6-bis-(di-n-propylamino-acetylamino)-4-hydroxycarbonyl-benzo[1,2-d:5,4-d']bisthiazole,
2,6-bis-(dimethylamino-acetylamino)-4-chloro-8-hydroxycarbonyl-benzo[1,2-d:5,4-d']bisthiazole,
2,6-bis(dimethylamino-acetylamino)-4-chloro-8-acetyl-benzo[1,2-d:5,4-d']-bisthiazole,
2-(diethylamino-acetylamino)-6-(piperidino-acetylamino)benzo[1,2-d:5,4-d']bisthiazole,
2,6-bis-(dimethylamino-acetylamino)-4-methyl-8-hydroxycarbonyl-benzo[1,2-d:5,4-d']bisthiazole,
2,6-bis-(dimethylamino-acetylamino)-4-chloro-8-cyano-benzo[1,2-d:5,4-d']bisthiazole,
2,6-bis-(dimethylamino-acetylamino)-4-chloro-8-phenyl-benzo[1,2-d:5,4-d']bisthiazole,
2,6-bis-(dimethylamino-acetylamino)-4-chloro-8-methyl-benzo[1,2-d:5,4-d']bisthiazole,
2,6-bis-(dimethylamino-acetylamino)-4-chloro-8-aminocarbonyl-benzo[1,2-d:5,4-d']bisthiazole,
2,6-bis-(cyclohexylamino-acetylamino)-benzo[1,2-d:5,4-d']bisthiazole,
2,6-bis-[N'-ethyl-N'-(N,N-diethylamino-acetyl)-amino]-benzo[1,2-d:5,4-d']bisthiazole,
2,6-bis-(diethylamino-acetylamino)-4-nitro-benzo[1,2-d:5,4-d']bisthiazole, and
2,6-bis-(diethylamino-acetylamino)-4-methyl-8-chloro-benzo[1,2-d:5,4-d']bisthiazole.

The following examples illustrate the present invention and will enable others skilled in the art to understand it more completely. It should be understood, however, that the invention is not limited solely to the particular examples given below.

EXAMPLE 1

2,6-Bis(diethylamino-acetylamino)-benzo[1,2-d:5,4-d']bisthiazole by method A

A mixture consisting of 23 gm of 2,6-bis-chloroacetylamino)-benzo[1,2-d:5,4-d']bisthiazole (M.P. 330° C.), 30 gm of diethylamine and 100 ml of dimethylformamide was heated in a pressure vessel overnight at 100° C. Thereafter, the reaction mixture was allowed to cool, was then poured into 500 ml of water, and the aqueous mixture was extracted four times with 300 ml of chloroform. The combined chloroform extracts were washed with water and then evaporated in vacuo. This residue (19 gm) was treated with 20 ml of chloroform, the chloroform-insoluble matter was filtered off, and the filtrate was chromatographed on a 500 gm-silicagel column with chloroform/methanol (97:3), yielding 9 gm (33% of theory) of the base of the formula

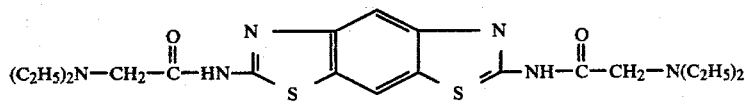

which had a melting point of 223°–225° C. after recrystallization from ethanol.

Its dihydrochloride was obtained by adding an excess of ethereal hydrochloric acid to a solution of the base in chloroform. Recrystallized successively from dioxane (water and methanol, the dihydrochloride had a melting point of <270° C. (decomp.).

EXAMPLE 2

2-Amino-6-(diethylamino-acetylamino)-benzo[1,2-d:5,4-d']bisthiazole

The chloroform-insoluble matter filtered off in Example 1 was recrystallized from ethanol/dimethylformamide, yielding 2.5 gm (12% of theory) of the compound of the formula

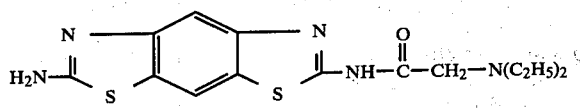

which had a melting point of 203°–205° C.

EXAMPLE 3

The procedures described in Examples 1 and 2 were repeated, but the reaction of Example 1 was carried out by refluxing the reactants in ethanol. 25% of theory of the 2,6-bis-(diethylamino-acetylamino)-substituted base and 18% of theory of the 2-amino-6-(diethylamino-acetylamino)-substituted base were obtained.

EXAMPLE 4

A mixture consisting of 3.7 gm of 2,6-bis-(chloroacetylamino)-benzo[1,2-d:5,4-d']bisthiazole, 5 gm of diethylamine and 50 ml of dioxane was refluxed for two hours. Thereafter, the reaction mixture was evaporated in vacuo, the residue was dissolved in 5 ml of chloroform, and the solution was washed with water, dried over sodium sulfate and chromatographed on a 100 gm-silicagel column with chloroform as the flow agent. The eluate fractions were tested by thin-layer chromatography with chloroform/methanol (97:3). The main fraction yielded 2.8 gm (63.3% of thoery) of the base end product of Example 1, which had a melting point of 223°–225° C. after recrystallization from ethanol.

The base was re-dissolved in chloroform, and an excess of ethereal hydrochloric acid was added to the solution, yielding 3.0 gm of the hydrochloride M.P.<270° C. (decomp.).

The starting compound was obtained as follows:

(a) 20 ml of chloroacetyl chloride were added to a suspension of 15 gm of 2,6-diamino-benzo[1,2-d:5,4-d']bisthiazole in 130 ml of dimethylformamide at 10° C., while vigorously stirring. The resulting mixture was heated for one hour on a water bath, then cooled and filtered, and the filter cake was washed with benzene and dried. 24 gm of 2,6-bis-(chloroacetyl-amino)-benzo[1,2-d:5,4-d']bisthiazole, m.p. 330° C. (recrystallized from dimethylformamide/water), were obtained.

(b) A mixture consisting of 222 mgm of 2,6-diamino-benzo[1,2-d:5,4-d']bisthiazole, 500 mgm of p-nitro-phenyl chloroacetate and 5 ml of dioxane were refluxed for 15 minutes. The reaction mixture was allowed to cool, and the crystalline substance which had separated out was filtered off, washed and dried. 350 mgm (93% of theory) of 2,6-bis-(chloroacetyl-amino)-benzo[1,2-d:5,4-d']bisthiazole, M.P. 330° C., were obtained.

(c) A mixture consisting of 222 mgm of 2,6-diamino-benzo[1,2-d:5,4-d']bisthiazole, 513 mgm of chloroacetic acid anhydride and 2 ml of dry dimethyl-formamide was refluxed for 10 minutes. The resulting suspension was admixed with ethanol, and the crystalline substance which separated out was washed and dried. 300 mgm (80% of theory) of 2,6-bis-(chloroacetyl-amino)-benzo[1,2-d:5,4-d']bisthiazole were obtained.

EXAMPLE 5

2,6-Bis-[N'-methyl-N'-(N,N-diethylamino-acetyl)-amino]benzo[1,2-3:5,4-d']bisthiazole by method A A stirred mixture consisting of 10 gm of 2,6-bis-[N'-methyl-N'-chloroacetyl-amino)-benzo[1,2-d:5,4-d']bisthiazole, 10 gm of diethylamine and 100 ml of dioxane was heated at 100° C. in a pressure vessel overnight. Thereafter, the reaction mixture was evaporated in vacuo, the residue was dissolved in chloroform, and the solution was washed with water, dried and evaporated to dryness. The residue was recrystallized three times from dimethylformamide, yielding 5.0 gm (42% of theory) of the compound named in the heading, which had a melting point of 267°–269° C.

The base was dissolved in chloroform, ethereal hydrochloric acid was added to the solution, and the hydrochloride precipitated thereby was collected, washed and dried, it had a melting point of 244°–246° C.

The starting compound was obtained as follows:

8 ml of chloroacetyl chloride were added to a stirred, ice-cooled suspension of 6.5 gm of 2,6-bis-(dimethylamino)-benzo[1,2-d:5,4-d']bisthiazole in 50 ml of dimethylformamide. The resulting mixture was heated at 90° C. for 90 minutes and was then poured into water. The precipitate formed thereby was filtered off, washed and dried, yielding 10 gm (95% of theory) of 2,6-bis-[N'-methyl-N'-chloroacetyl-amino]benzo[1,2-d:5,4-d']bisthiazole which had a melting point of 250° C. (decomp.) after recrystallization from dimethylformamide.

The following compounds were prepared in analogous manner.

2,6-Bis-[N'-ethyl-N'-(N,N-diethylamino-acetyl)-amino]-benzo[1,2-d:5,4-d']bisthiazole, M.P. 133°–135° C.;

2,6-bis[N'-ethyl-N'-(N,N-diethylamino-acetyl)-amino]-4-bromo-benzo[1,2-d:5,4-d']bisthiazole, m.p. 158°–160° C.

EXAMPLE 6

2,6-Bis-(piperidinoacetyl-amino)-benzo[1,2-d:5,4-d']bisthiazole dihydrochloride 1.5 H₂O by method A (a) A mixture consisting of 7.5 gm of 2,6-bis-(chloroacetyl-amino)-benzo[1,2-d:5,4-d']bisthiazole, 14 gm of piperidine and 50 ml of dioxane was heated at 90° C. for 8 hours. The cooled reaction mixture was admixed with 25 ml of water and 100 ml of ethyl acetate. The resulting precipitate was washed and recrystallized first from ethanol in the presence of several drops of hydrochloric acid, and then from ethanol/water.

Yield: 4.0 g (37% of theory) of the title compound, M.P. 293°–295° C.

(b) A mixture consisting of 0.9 gm of 2,6-bis-(chloroacetyl-amino)-benzo[1,2-d:5,4-d']bisthiazole, 2 gm of piperidine and 5 ml of dimethylformamide was heated for 15 hours on a water-bath. Then, the reaction mixture was evaporated in vacuo, and the residue was treated with ethereal hydrochloric acid. The precipitate formed thereby was recrystallized twice from water.

Yield: 0.9 gm (68% of theory) of the title compound, M.P. 292°–295° C.

The following compounds were obtained in analogous manner:

2,6-bis-(pyrrolidino-acetylamino)-benzo[1,2-d:5,4-d']bisthiazole, M.P. 290°–292° C.;

2,6-bis-(thiazolidino-acetylamino)-benzo[1,2-d:5,4-d']bisthiazole, M.P. 263°–265° C.;
2,6-bis-(thiomorpholino-acetylamino)-benzo[1,2-d:5,4-d']bisthiazole, M.P. 303°–305° C.;
2,6-bis-(4-phenylpiperidino-acetylamino)-benzo[1,2-d:5,4-d']bisthiazole, M.P. 303°–305° C.;
2,6-bis-(4-phenylpiperidino-acetylamino)-benzo[1,2-d:5,4-d']bisthiazole, M.P. 288°–290° C.
2,6-bis-(morpholino-acetylamino)-benzo[1,2-d:5,4-d']bisthiazole, m.p. 280° C.
2,6-bis-(piperidino-piperidino-acetylamino)-benzo[1,2-d:5,4-d']bisthiazole, M.P. 272°–274° C.;
2,6-bis-(3',5'-dimethylpiperidino-acetylamino)-benzo[1,2-d:5,4-d']bisthiazole, M.P. 262°–265° C.
2,6-bis-(4-benzylpiperidino-acetylamino)-benzo[1,2-d:5,4-d']bisthiazole, M.P. 233°–235° C.;
2,6-bis-(2-ethoxycarbonylpiperidino-acetylamino)-benzo[1,2-d:5,4-d']bisthiazole, M.P. 138°–140° C.

EXAMPLE 7

2,6-Bis-[(N-methyl-N-cyclohexyl-amino)-acetylamino]-benzo[1,2-d:5,4-d']bisthiazole dihydrochloride 1.5 H$_2$O by Method A A stirred mixture consisting of 9.0 gm of 2,6-bis-(chloroacetyl-amino)-benzo[1,2-d:5,4-d']bisthiazole, 20.0 gm of N-methyl N-cyclohexyl-amine and 100 ml of dioxane was heated for 8 hours on a waterbath. Afterwards, the reaction mixture was evaporated in vacuo and chloroform and water were added to the residue.

The organic phase was washed, dried and evaporated. 14 gm of residue were obtained, the latter being chromatographed on a 400 gm-silicagel column with chloroform as the mobile phase. The eluted product (6.8 gm = 58% of theory) was treated in chloroform with ethereal hydrochloric acid, and the resulting hydrochloride was washed and dried.

Yield: 7 gm of the hydrochloride, M.P. 230°–235° C.

The following compounds were produced in analogous manner:
2,6-bis[(N-methyl-N-cyclooctyl-amino)-acetylamino]-benzo[1,2-d:5,4-d']bisthiazole, M.P. 137°–139° C.;
2,6-bis-[(N-methyl-N-cyclopentyl-amino)-acetylamino]benzo[1,2-d:5,4-d']bisthiazole, M.P. 189°–191° C.

EXAMPLE 8

2,6-Bis-(diethylamino-acetylamino)-4-chloro-8-trifluoromethyl-benzo[1,2-d:5,4-d']bisthiazole dihydrochloride by method A A stirred mixture of 8.5 gm of 2,6-bis-(chloroacetylamino)-4-chloro-8-trifluoromethyl-benzo[1,2-d:5,4-d']bisthiazole, 11 gm of diethylamine and 100 ml of dioxane was heated at 100° C. in a closed vessel for 4 hours. The reaction mixture was then evaporated in vacuo, the residue was dissolved in chloroform, and the solution was washed and then dried over sodium sulfate. Upon evaporation, 7.5 gm of the crude product were obtained. It was redissolved and chromatographed on a 220 gm-silicagel column with chloroform as the mobile phase. The main fraction was treated with ethereal hydrochloric acid, and the precipitated hydrochloride was washed and dried.

Yield: 6.0 (54% of theory); M.P. 240°–245° C. (decomp.).

The starting compound was obtained as follows: 10 ml of chloroacetyl chloride were added to a stirred mixture of 6 gm of 2,6-diamino-4-chloro-8-trifluoromethyl-benzo[1,2-d:5,4-d']bisthiazole and 100 ml of dimethylformamide while cooling. The resulting mixture was heated for one hour at 60° C. and was then allowed to stand overnight. The resulting precipitate was recrystallized from dimethylformamide.

Yield: 8.5 gm (96% of theory); M.P. >350° C.

The 2,6-diamino-4-chloro-8-trifluoromethyl-benzo[1,2-d:5,4-d']bisthiazole, M.P. >340° C., was obtained by reacting a cooled mixture of 2-chloro-5-trifluoromethyl-m-phenylene-diamine (see German Offenlegungsschrift 2,025,896) and potassium thiocyanate in acetic acid and methanol with a solution of bromine in acetic acid.

EXAMPLE 9

2,6-Bis-(diethylamino-acetylamino)-4-chloro-8-cyano-benzo[1,2-d:5,4-d']bisthiazole dihydrochloride by method A.

A mixture of 8 gm of 2,6-bis-(chloroacetyl-amino)-4-chloro-8-cyano-benzo[1,2-d:5,4-d']bisthiazole, 10 gm of diethylamine and 100 ml of dioxane was reacted as described in Example 8.

Yield: 3.8 gm (35% of theory) of the title compound, M.P. 260°–265° C.

The starting compound was produced as follows:
4 ml of chloroacetyl chloride were added to a stirred suspension of 2.6 gm of 2,6-diamino-4-chloro-8-cyano-benzo[1,2-d:5,4-d']bisthiazole in 30 ml of dimethyl-formamide at 10° C. The resulting mixture was heated at 80° C. for 4 hours, cooled, and the precipitate was recrystallized from dimethylformamide. The obtained 2,6-bis-(chloroacetyl-amino)-4-chloro-8-cyano-benzo[1,2-d:5,4-d']bisthiazole melted at >330° C.;

Yield: 2.3 gm (58% of theory).

The 2,6-diamino-4-chloro-8-cyano-benzo[1,2-d:5,4-d']bis-thiazole, M.P. 350° C., was obtained by reacting 2-chloro-5-cyano-m-phenylene-diamine (see German Offenlegungsschrift 2,025,896) and potassium thiocyanate in acetic acid and methanol with a solution of bromine in acetic acid.

The following compounds were prepared in analogous manner:
2,6-bis-(diethylamino-acetylamino)-4,8-dichloro-benzo[1,2-d:5,4-d']bisthiazole, M.P. 278°–280° C.;
2,6-bis-(diethylamino-acetylamino)-4-methyl-8-chloro-benzo[1,2-d:5,4-d']bisthiazole, M.P. 245°–247° C.;
2,6-bis-(diethylamino-acetylamino)-4-nitro-benzo[1,2-d:5,4-d']bisthiazole, M.P. 276°–278° C.;
2,6-bis-(diethylamino-acetylamino)-4-bromo-benzo[1,2-d:5,4-d']bisthiazole, M.P. 192°–194° C.
2,6-bis-(diethylamino-acetylamino)-4-chloro-benzo[1,2-d:5,4-d']bisthiazole, M.P. 212°–215° C.;
2,6-bis-(diethylamino-acetylamino)-8-methoxy-benzo[1,2-d:5,4-d']bisthiazole, M.P. 176°–178° C.;
2,6-bis-(diethylamino-acetylamino)-4-methoxy-benzo[1,2-d:5,4-d']bisthiazole, M.P. 175°–177° C.;
2,6-bis-(diethylamino-acetylamino)-8-bromo-benzo[1,2-d:5,4-d']bisthiazole, M.P. 196°–198° C.;
2,6-bis-(diethylamino-acetylamino)-4-chloro-8-methoxy-benzo[1,2-d:5,4-d']bisthiazole, M.P. 172°–174° C.;
2,6-bis-(diethylamino-acetylamino)-3-ethoxycarbonyl-benzo[1,2-d:5,4-d']bisthiazole, M.P. 215°–217° C.;
2,6-bis-(diethylamino-acetylamino)-4-methyl-8-ethoxycarbonylbenzo[1,2-d:5,4-d']bisthiazole, M.P. 256°–257° C.;

2,6-bis-(diethylamino-acetylamino)-4-chloro-8-phenyl-benzo[1,2-d:5,4-d']bisthiazole, M.P. 247°-249° C.;

2,6-bis-(diethylamino-acetylamino)-4-chloro-8-ethoxycarbonylbenzo[1,2-d:5,4-d']bisthiazole, M.P. 268°-270° C.;

2,6-bis-(diethylamino-acetylamino)-4-bromo-8-chloro-benzo[1,2-d:5,4-d']bisthiazole, m.p. 265°-267° C.;

2,6-bis-(diethylamino-acetylamino)-4-amino-benzo[1,2-d:5,4-d']bisthiazole, M.P. 160°-162° C.;

2,6-bis-(diethylamino-acetylamino)-4-chloro-8-bromo-benzo[1,2-d:5,4-d']bisthiazole, M.P. 278°-280° C.

EXAMPLE 10

2,6-Bis-(diethylamino-acetylamino)-benzo[1,2-d:5,4-d']bisthiazole by method B (a) 0.5 gm of sodium hydride was added to a solution of 1.1 gm of 2,6-diamino-benzo[1,2-d:5,4-d']bisthiazole and 1.6 gm of ethyl N,N-diethyl-glycinate in 5 ml of dimethylsulfoxide, and the mixture was stirred overnight at room temperature. Then, water was added and the mixture was extracted with chloroform. The residue remaining after evaporation of the dried chloroform extracts was chromatographed on a 30 gm silicagel column with chloroform as the mobile phase. 0.5 gm (23% of theory) of the title compound, M.P. 224°-225° C., were obtained from the second fraction.

(b) A solution of 222 mgm of 2,6-diamino-benzo[1,2-d:5,4-d']bisthiazole and 600 mgm of diethylglycine phenyl ester in 5 ml of dimethylformamide was refluxed for 1 hour while stirring. The reaction mixture was worked up as described in Examples 1 and 2. 200 mgm (44.5% of theory) of 2,6-bis-(diethylamino-acetylamino)-benzo[1,2-d:5,4-d']bisthiazole, M.P. 223°-225° C., and 150 mgm (57% of theory) of 2-amino-6-(diethylamino-acetylamino)-benzo[1,2-d:5,4-d]bisthiazole, M.P. 204°-205° C. were obtained.

EXAMPLE 11

2,6-Bis-(diethylaminoacetylamino)-benzo[1,2-d:5,4-d']bisthiazole by method B 1.0 gm of ethyl-3-(3-diethylamino-propyl)-carbodiimide was added to a suspension of 555 mgm of 2,6-diamino-benzo[1,2-d:5,4-d']bisthiazole and 655 mgm of N,N-diethyl-glycine in 20 ml of methylene chloride, and the mixture was stirred overnight at room temperature. After adding water and filtering off the precipitate, the methylene chloride phase was separated, dried, concentrated and chromatographed on a dry 10 gm-silicagel column with chloroform as the mobile phase. The title compound was collected in the first fractions and converted into the dihydrochloride by treatment with ethereal hydrochloric acid.

Yield: 48 mgm (3.6% of theory), M.P. >270° C. (decomp.).

EXAMPLE 12

2,6-Bis-(diethylamino-acetylamino)-4-methyl-benzo[1,2-d:5,4-d']bisthiazole by method A 20 gm of diethylamine were added to 11.5 gm of 2,6-bis-(chloroacetyl-amino)-4-methyl-benzo[1,2-d:5,4-d']bisthiazole in 80 ml of dioxane and the mixture was boiled for 3 hours. Then it was evaporated to dryness in vacuo, and the residue (12 gm) was chromatographed on a dry 300 gm-silicagel column with benzene/chloroform (1:1) as the mobile phase. The title compound was obtained first; 9.0 gm (66% of theory), melting point 191°-192° C., were obtained after recrystallization from alcohol.

The dihydrochloride M.P. 225° C. (decomp.) was obtained from a chloroform solution of the base with an excess of ethereal hydrochloric acid.

The starting compound was produced as follows:

A solution of 6 gm of 2,6-diamino-4-methyl-benzo[1,2-d:5,4-d']-bisthiazole in 50 ml of dimethylformamide was admixed at 5° C. with 10 ml of chloroacetyl chloride. The mixture was heated for two hours on a waterbath. Upon cooling, 2,6-bis-(chloro-acetylamino)-4-methyl-benzo[1,2-d:5,4-d']bisthiazole crystallized out; it was washed and recrystallized from dimethylformamide.

Yield: 6.5 gm (66% of theory), M.P. 330° C.

The following compounds were produced analogously:

2,6-bis-(diethylamino-acetylamino)-8-methoxy-benzo[1,2-d:5,4-d']bisthiazole, M.P. 176°-178° C.;

2,6-bis-(diethylamino-acetylamino)-4-methoxy-benzo[1,2-d:5,4-d']bisthiazole, M.P. 175°-177° C.

EXAMPLE 13

2-(Diethylamino-acetylamino)-6-(piperidino-acetylamino)benzo[1,2-d:5,4-d']bisthiazole by method A (a)

2-Chloroacetylamino-6-amino-benzo[1,2-d:5,4-d']bisthiazole 1.2 gm of chloroacetyl chloride were added to a stirred solution of 2.2 gm of 2,6-diamino-benzo[1,2-d:5,4-d']bisthiazole in 20 ml of dimethylformamide at 5° C. The resulting suspension was heated for 1 hour on a waterbath, then cooled, and the solid 2,6-bis-(chloroacetyl-amino)-benzo[1,2-d:5,4-d']bisthiazole was filtered off. While stirring, 0.5 gm of an aqueous saturated sodium carbonate solution was added to the filtrate. After 1 hour the precipitate was filtered off, dissolved in 30 ml of dimethylformamide/dioxan (1:1), freed from traces of insoluble material and precipitated again with water. The crystals were dissolved in dimethylformamide and the solution was treated with an excess of 2 N hydrochloric acid. The hydrochloride obtained thereby was washed and dried.

Yield: 1.0 gm (30% of theory), m.p. 300° C.

(b)

2-(Diethylamino-acetylamino)-6-amino-benzo[1,2-d:5,4-d']bisthiazole

A mixture of 0.5 gm of 2-(chloroacetyl-amino)-6-amino-benzo[1,2-d:5,4-d']bisthiazole, 0.7 gm of diethylamine and 3 ml of dioxane was refluxed for 2 hours. Then, the solvent was evaporated in vacuo, the residue was dissolved in ethyl acetate, and the solution was washed with water and dried over sodium sulfate. After evaporation of the solvent, 0.3 gm (60% of theory) of the title compound, M.P. 203°-205° C. (from ethanol/dimethylformamide) were obtained.

(c)

2-(Diethylamino-acetylamino)-6-(chloroacetylamino)-benzo[1,2-d:5,4-d']bisthiazole 500 mgm of chloroacetyl chloride were added to a stirred solution of 950 gm of 2-(diethylamino-acetylamino)6-amino-benzo[1,2-d:5,4-d']bisthiazole in 5 ml of dimethylformamide at 0° to 5° C. The mixture was heated for 30 minutes on a waterbath, then cooled, admixed with 50 ml of water and made alkaline with pyridine. The resulting precipitate was collected, washed and recrystallized from dimethylformamide.

Yield: 500 mgm (43% of theory), M.P. 280°–282° C.

(d) 6 gm of piperidine were added to a solution of 5.0 gm of 2-(diethylamino-acetylamino)-6-(chloroacetylamino)-benzo[1,2-d:5,4-d']bisthiazole in 70 ml of dioxane, and the mixture was refluxed for 2 hours. The residue obtained by evaporation of the reaction solution was in vacuo was dissolved in chloroform, and the solution was chromatographed on a dry 150 gm-silicagel column with chloroform as the mobile phase. The first fraction is collected, the base (4.6 gm, M.P. 221°–223° C., from acetonitrile) was dissolved in chloroform, and the hydrochloride was precipitated with excess ethereal hydrochloric acid.

Yield: 5.0 gm (70% of theory), M.P. 280° C. (decomp.).

The following compound was produced analogously: 2-(diethylamino-acetylamino)-6-(chloroacetyl-amino)-benzo[1,2-d:5,4-d']bisthiazole, M.P. 280°–282° C.

EXAMPLE 14

2,6-Bis-(dimethylamino-acetylamino)-benzo[1,2-d:5,4-d']bisthiazole by method B 5 gm of a 50% suspension of sodium hydride in oil was added in portions to a stirred solution of 11 gm of 2,6-diamino-benzo[1,2-d:5,4-d']bisthiazole and 14 gm of ethyl N,N-diethylglycinate in 50 ml of dimethylsulfoxide in an atmosphere of nitrogen. The mixture was kept at 5° to 10° C. in the meantime. Then, the mixture was allowed to stand overnight at room temperature, was then poured into 600 ml of water, and the mixture was extracted with chloroform. The aqueous phase was neutralized with dilute hydrochloric acid, and the precipitated free base was filtered off and recrystallized from ethanol/dimethylformamide (1:1).

Yield: 6.5 gm (33% of theory); m.p. 288°–290° C.

Recrystallization from ethanol/water (4:1) in the presence of an excess of concentrated hydrochloric acid yielded the corresponding dihydrochloride, m.p. 270°–273° C. (decomp.).

EXAMPLE 15

2,6-Bis-(ethylamino acetylamino)-benzo[1,2-d:5,4-d']bisthiazole dihydrochloride by method B 7.3 gm of a 50% sodium hydride suspension in oil were added in portions to an ice-cooled and stirred mixture of 16 gm of 2,6-diamino-benzo[1,2-d:5,4-d']bisthiazole, 20.5 gm of ethyl N-ethyl-glycinate and 75 ml of dimethylsulfoxide at a rate such that the temperature could be kept between 5° to 10° C. The mixture is allowed to stand overnight at room temperature, was then poured into 200 ml of water, and the aqueous solution was neutralized with concentrated hydrochloric acid. The precipitate formed thereby was collected and treated with 200 ml of boiling dimethylformamide, the resulting suspension was filtered while hot, and the filter cake was recrystallized from ethanol/2 N hydrochloric acid (9:1).

Yield: 3.7 gm (11.3% of theory) of the title compound, M.P. 230°–250° C. (decomp.).

EXAMPLE 16

2,6-Bis-(di-n-propylamino-acetylamino)-benzo[1,2-d:5,4-d']bisthiazole dihydrochloride by method A A mixture of 7.2 gm of 2,6-bis-(chloroacetyl-amino)-benzo[1,2-d:5,4-d']bisthiazole, 10 gm of di-n-propylamine and 100 ml of dioxane was refluxed for two hours and then evaporated to dryness in vacuo. The residue was dissolved in chloroform, and the solution was washed with water, dried, evaporated to a small volume and chromatographed on a 300 gm silicagel column with chloroform and chloroform/methanol (95:5) as the mobile phase. The title compound, 2.5 gm (25.5% of theory), was eluted, dissolved in chloroform, treated with gaseous hydrogen chloride, and the collected hydrochloride was recrystallized from ethanol/water. M.P. 210° C.

EXAMPLE 17

2-Amino-6-(di-n-propylamino-acetylamino)-benzo[1,2-d:5,4-d']bisthiazole

Subsequent to the elution of the title compound in Example 16, the monoacetylated analog was precipitated and crystallized from ethanol.

M.P. 155°–157° C.

The following compounds were produced analogously;

2,6-bis-(hexamethyleneimino-acetylamino)-benzo[1,2-d:5,4-d']bisthiazole, M.P. 245°–247° C.;
2,6-bis-(4-methylcyclohexylamino-acetylamino)-benzo[1,2-d:5,4-d']bisthiazole, m.p. 250°–252° C.;
2,6-bis-(cycloheptylamino-acetylamino)-benzo[1,2-d:5,4-d']bisthiazole, M.P. 240°–242° C.;
2,6-bis-(cyclohexylamino-acetylamino)-benzo[1,2-d:5,4-d']bisthiazole, m.p. 257°–259° C.:
2,6-bis-(cyclopentylamino-acetylamino)-benzo[1,2-d:5,4-d']bisthiazole, M.P. 258°–260° C.;
2,6-bis-(cyclopropylamino-acetylamino)-benzo[1,2-d:5,4-d']bisthiazole, m.p. 203°–205° C.:
2,6-bis-(3'-methyl-cyclopentylamino-acetylamino)-benzo[1,2-d:5,4-d']bisthiazole, m.p. 220°–222° C.;
2,6-bis-(2'-methyl-cyclopentylamino-acetylamino)-benzo[1,2-d:5,4-d']bisthiazole, m.p. 238°–240° C.

EXAMPLE 18

(a)
2,6-Bis-N-carbethoxypiperazino-acetylamino)-benzo[1,2-d:5,4-d']bisthiazole (b)
2-Amino-6-(N-carbethoxypiperazino-acetylamino)-benzo[1,2-d:5,4-d']bisthiazole A mixture of 7.5 gm of 2,6-bis-(chloroacetyl-amino)-benzo[1,2-d:5,4-d']bisthiazole, 7 gm of ethyl N-piperazinocarboxylate, 4 gm of triethylamine and 250 ml of dioxane was refluxed for one hour, and the reaction mixture was worked up in the manner described in Example 16.

There are isolated 5.2 gm (43.5% of theory) of the title compound (a), M.P. 238°–240° C.; dihydrochloride.1.5H$_2$O, M.P. 225° C. (decomp.) and 2.0 gm (24% of theory) of the title compound (b), M.P. 228°–230° C. (from ethanol).

The following compound was produced analogously: 2,6-bis[N-ethoxycarbonylmethyl)-piperazino-acetylamino]benzo[1,2-d:5,4-d']bisthiazole, M.P. 158°–160° C.

EXAMPLE 19

2,6-Bis-[N-(β-hydroxyethyl)-piperazino-acetylamino]-benzo[1,2-d:5,4-d']bisthiazole dihydrochloride.1.5H$_2$O by method A

A mixture of 9.5 gm 2,6-bis-(chloroacetyl-amino-benzo[1,2-d:5,4-d']bisthiazole, 16 gm of N-(β-hydroxyethyl)piperazine and 200 ml of dioxane was refluxed for 2 hours. Then, the reaction mixture was evaporated to dryness, and the residue was recrystallized twice from dimethylformamide. The free base, m.p. 238°-240° C. thus obtained, was converted in the conventional way into the corresponding dihydrochloride .1.5H$_2$O, M.P. 265°-270° C. (decomp.).

Yield: 8.0 gm (47.5% of theory).

The following compound was produced analogously:
2,6-bis[N-(2,2,2-trifluoroethyl)-piperazino-acetylamino]benzo[1,2-d:5,4-d']bisthiazole, M.P. 270°-275° C. (decomp.)

EXAMPLE 20

(a)
2,6-Bis-(3-methylpiperidino-acetylamino)-benzo[1,2-d:5,4-d']bisthiazole

(b)
2-Amino-6-(3-methylpiperidino-acetylamino)-benzo[1,2-d:5,4-d']bisthiazole monohydrate

A mixture of 8.0 gm of 2,6-bis-(chloroacetyl-amino)-benzo[1,2-d:5,4-d']bisthiazole, 9.0 gm of 3-methylpiperidine and 100 ml of dioxane was refluxed for 2 hours. The reaction mixture was worked up as described in Example 16.

Yield: 5.0 gm (47% of theory) of compound (a), M.P. 240°-242° C. (from ethanol/dimethylformamide) and 3.8 gm (47% of theory) of compound (b), M.P. 184° C. (from ethanol).

EXAMPLE 21

(a)
2,6-Bis-(2-ethylpiperidino-acetylamino)-benzo[1,2-d:5,4-d']bisthiazole

(b)
2-Amino-6-(2-ethylpiperidino-acetylamino)-benzo[1,2-d:5,4-d']bisthiazole

A mixture of 8.0 gm of 2,6-bis-(chloroacetyl-amino)-benzo[1,2-d:5,4-d']bisthiazole, 10.0 gm of 2-ethyl-piperidine and 100 ml of dioxane was refluxed for 2 hours. The reaction mixture was worked up as described in Example 16; the compounds (a) (47% of theory, from ethanol), M.P. 201°-203° C., and (b) (37% of theory, from ethanol), M.P. 223°-225° C, were isolated.

The following compounds were produced analogously:
2,6-bis-(2-hydroxymethylpiperidino-acetylamino)-benzo[1,2-d:5,4-d']bisthiazole, M.P. 226°-228° C.;
2,6-bis[2-(β-hydroxyethyl)-piperidino-acetylamino]-benzo[1,2-d:5,4-d']bisthiazole, M.P. 185°-187° C.;
2,6-bis-[2-(cyclohexyl-methyl)-piperidino-acetylamino]-benzo[1,2-d:5,4-d']bisthiazole, M.P. >110° C. (decomp.).

EXAMPLE 22

(a)
2,6-Bis-[1-(p-fluorophenyl)-piperazino-acetylamino]-benzo[1,2-d:5-4-d']bisthiazole

(b)
2-Amino-6-[1-(p-fluorophenyl)-piperazino-acetylamino]benzo[1,2-d:5,4-d']bisthiazole

A mixture of 9.0 gm of 2,6-Bis-(chloroacetyl-amino)-benzo[1,2-d:5,4-d']bisthiazole, 9.0 gm of 1-(p-fluorophenyl)piperazine, 5.0 gm of triethylamine and 200 ml of dioxane was refluxed for 2 hours. Then, the reaction mixture was evaporated, the residue was treated with chloroform and water, and the insoluble matter was collected and recrystallized from dimethylformamide.

5.3 gm (33% of theory) of compound (a), M.P. 268°-270° C. (from dimethylformamide/ethanol), were obtained.

The chloroform filtrate was dried and evaporated to dryness, leaving 9.0 gm of residue which was treated with 50 ml of chloroform. By filtering, 1.6 gm of solid substance identical to compound (a) were obtained; the filtrate was chromatographed on a 100 gm silicagel column with chloroform and chloroform/methanol (95:5) as the mobile phases. The first fraction (1.5 gm) was identical to compound (a) (combined yield of 54% of theory). The second fraction (1.1 gm 10.5% of theory) corresponds to the monoacylated analog (b), M.P. 230° C. (from ethanol, chloroform).

In the same manner the following compounds were produced:
2,6-bis[1-(p-chlorophenyl)-piperazino-acetylamino]benzo[1,2-d:5,4-d']bisthiazole, M.P. 225°-227° C.;
2,6-bis-(N-phenylpiperazino-acetylamino)-benzo[1,2-d:5,4-d']bisthiazole, M.P. 293°-295° C.;
2,6-bis[N-(3-trifluoromethylphenyl)-piperazino-acetylamino]benzo[1,2-d:5,4-d']bisthiazole, M.P. 232°-234° C.;
2,6-bis-(2',5'-dimethylpiperazino-acetylamino)-benzo[1,2-d:5,4-d']bisthiazole tetrahydrochloride, M.P. 260° C. (decomp.);
2,6-bis[N-(4'-acetylphenyl)-piperazino-acetylamino]-benzo[1,2-d:5,4-d']bisthiazole hydrochloride, M.P. >300° C.;
2,6-bis[N-(pyridyl-(2)-piperazino-acetylamino]-benzo[1,2-d:5,4-d']bisthiazole, M.P. 285° C. (decomp.);
2,6-bis-(N-benzylpiperazino-acetylamino)-benzo[1,2-d:5,4-d']bisthiazole, M.P. 247°-249° C.

EXAMPLE 23

(a)
2,6-Bis-(4-methylpiperidino-acetylamino)-benzo[1,2-d:5,4-d']bisthiazole

(b)
2-Amino-6-(4-methylpiperidino-acetylamino)-benzo[1,2-d:5,4-d']bisthiazole

A mixture of 8.0 gm of 2,6-bis-(chloroacetyl-amino)-benzo[1,2-d:5,4-d']bisthiazole, 9.0 gm of 4-methylpiperidine and 100 ml of dioxane was refluxed for 2 hours, and the reaction mixture was worked up as described before, see Example 16. Two products were isolated:

Title compound (a) 6.0 gm (40.5% of theory), M.P. 245°-247° C. (from ethanol);
Title compound (b) 3.6 gm (34% of theory), m.p. 155°-159° C. (from ethanol).

2,6-Bis-(2-methylpiperidino-acetylamino)-benzo[1,2-d:5,4-d']bisthiazole, M.P. 242°-245° C. was produced in analogous manner.

EXAMPLE 24

2,6-Bis-(4-methylpiperazino-acetylamino)-benzo[1,2-d:5,4-d']bisthiazole by method A A mixture of 8.0 gm of 2,6-bis-(chloroacetylamino)-benzo[1,2-d:5,4-d']bisthiazole, 9.0 gm of N-methylpiperazine and 100 ml of dioxane was refluxed for 2 hours. The reaction mixture was evaporated in vacuo to dryness, the residue was dissolved in chloroform, the solution was washed with water and dried, and the solvent was evaporated. The solid residue (10 gm) was recrystallized twice from ethanol.

Yield: 4.3 gm (40% of theory) of the title compound, M.P. 256°-258° C.

2,6-Bis-(piperazino-acetylamino)-benzo[1,2-d:5,4-d']bisthiazole, M.P. 230°-250° C. (decomp.), was obtained analogously.

EXAMPLE 25

2,6-Bis-(di-isopropylamino-acetylamino)-benzo[1,2-d:5,4-d']bisthiazole by method B 5 gm of a 50% sodium hydride suspension in oil were added to a mixture of 11 gm of 2,6-diamino-benzo[1,2-d:5,4-d']bisthiazole, 19 gm of ethyl N,N-di-isopropyl-glycinate and 50 ml of dimethylsulfoxide at 10° to 15° C. After the addition was finished, the mixture was stirred overnight at room temperature. 100 ml of water were added, the mixture was adjusted to pH 2 by adding 6 N hydrochloric acid, and it was then extracted with chloroform. The combined extracts were washed, dried and evaporated in vacuo. The residue was chromatographed on silicagel with chloroform and chloroform/methanol (95:5) as the mobile phases. The title compound (10 gm=39.6% of theory) was recrystallized from ethanol and melted at 255°-257° C.

The following compounds were prepared analogously:

2,6-bis-[di-(ethoxyethyl)-amino-acetylamino]benzo[1,2-d:5,4-d']bisthiazole, M.P. 82°-84° C.;

2,6-bis-(isopropylamino-acetylamino)-benzo[1,2-d:5,4-d']bisthiazole, M.P. 255°-257° C.

EXAMPLE 26

(a)
2,6-Bis-(anilino-acetylamino)-benzo[1,2-d:5,4-d']bisthiazole (b)
2-Amino-6-(anilino-acetylamino)-benzo[1,2-d:5,4-d']bisthiazole 1 gm of a 50% sodium hydride suspension in oil was added in portions to a stirred solution of 2.2 gm of 2,6-diamino-benzo[1,2-d:5,4-d']bisthiazole and 4.0 gm of ethyl N-phenyl-glycinate in 10 ml of dimethylsulfoxe at a temperature of 5°-10° C. The mixture was stirred overnight at room temperature, then poured into 200 ml of water, and neutralized with 6 N hydrochloric acid. The resulting precipitate was collected and recrystallized from pyridine.

Yield: 1.5 gm (30.8% of theory of title compound (a), M.P. 295°-297° C.

The mother liquor was evaporated to dryness, and the residue was recrystallized from ethanol. 1.1 gm of crystals were obtained, which were dissolved, while stirring, in 25 ml of a mixture of chloroform/methanol (9:1) and freed from the insoluble matter (600 mgm) by filtration.

The evaporated filtrate was chromatographed on a 30 gm-silicagel column with chloroform and chloroform/methanol (95:5) as the mobile phases, and the solvent was evaporated. After recrystallization from ethanol/chloroform, 2-amino-6-(anilino-acetylamino)-benzo[1,2-d:5,4-d']bisthiazole, M.P. 250° C. (decomp.) was obtained with a yield of 250 mgm.

EXAMPLE 27

2,6-Bis-(diethylamino-acetylamino)-benzo-[1,2-d:5,4-d']bisthiazole by method A

A mixture of 11.2 gm of 2,6-bis-(chloroacetyl-amino)-benzo[1,2-d:5,4-d']bisthiazole (M.P. 330° C.), 13.2 gm of diethylamino and 100 ml of 1,2-dichloro-ethane was refluxed for 2 hours. The reaction solution was cooled to room temperature, washed with water, dried and evaporated to dryness. The residue was recrystallized three times from ethanol. 5.3 gm of the title compound were obtained. The filtrate was evaporated to dryness, and the residue was admixed with 50 ml of boiling toluene. The insoluble portion, 1.4 gm of crude 2-amino-6-(diethylamino-acetylamino)-benzo[1,2-d:5,4-d']bisthiazole was filtered off, the filtrate was evaporated, and the residue was recrystallized three times from ethanol. An additional 1.9 gm of the pure title compound were obtained.

The total yield amounted to 7.2 gm (53.5% of theory), M.P. 223°-224° C.

EXAMPLE 28

2,6-Bis-(diethylamino-acetylamino)-benzo[1,2-d:5,4-d']bisthiazole by method B

A mixture of 2.2 gm of 2,6-diamino-benzo[1,2-d:5,4-d']bisthiazole, 4.8 gm of N,N-diethyl-glycine ethyl ester and 50 ml of a 0.6 N sodium ethylate solution was stirred at room temperature for 20 hours. Then the reaction mixture was evaporated, the residue was dissolved in water, and the solution was neutralized with about 15 ml of 2 N hydrochloric acid and extracted with chloroform. The extract was washed with water, dried and evaporated to dryness. The solid residue was recrystallized once from ethanol, yielding 2.8 gm 62.5% of theory of the title compound.

EXAMPLE 29

2,6-Bis-(diethylamino-propionylamino)-benzo[1,2-d:5,4-d']bisthiazole

A suspension of 5.5 gm of 2,6-diamino-benzo[1,2-d:5,4-d']bisthiazole, 13 gm of ethyl 2-(N,N-diethyl-amino)propionate and 125 ml of a 0.6 N sodium methylate solution was stirred at −6° C. for 20 hours. Afterwards, the mixture was evaporated to dryness in vacuo, the residue was dissolved in water, and the solution was neutralized with 37 ml of 2 N hydrochloric acid and extracted three times with chloroform. The combined extracts were washed, dried, and the solvent was evaporated. The residue was recrystallized three times from ethanol/dimethylformamide. 2.4 gm (22% of theory) of the title compound, M.P. 300°-320° C. (decomp.), were obtained.

Some of the 2,6-diamino-benzo[1,2-d:5,4-d']bisthiazole starting compounds of the formula III are described in the literature; see, for example, Barnikow et al., J. Prakt. Chemie 27, 271 (1965), and Landquist, J.

Chem. Soc. (C), 2212 (1967). Those not specifically described may be prepared by the processes there disclosed.

The starting compounds of the formula II, which are not described in the literature, may be prepared by reacting a 2,6-diamino-benzobisthiazole of the formula III with a haloacyl halide or anhydride or with a p-nitrophenyl halocarboxylate, preferably at elevated temperatures, as illustrated above.

The compounds of the present invention, that is, those embraced by formula I and their non-toxic, pharmacologically acceptable acid addition salts, have useful pharmacodynamic properties. More particularly, they exhibit antiarthritic and antirheumatic activities in warm-blooded animals, such as rats.

These properties were ascertained by the polyarthritis test according to Newbould, Brit. J. Pharmacol. 21, 137 (1963), and 24, 632 (1964).

Groups of 6 male rats of 150 to 160 gm body weight are used. Various doses of the test compounds are administered orally; for each 5 groups of treated animals, one group is left untreated as controls.

The perimeter of both hind paws is measured, and by means of intradermal injection of 0.2 ml of a suspension of dead tuberculosis bacilli in liquid paraffin (concentration 5 mg/ml) an arthritic syndrome is implanted into the surface of the left hind paw.

Administering of the daily dose of the test compounds is continued until the 14th day, and the perimeter of the hind paws is measured at certain intervals. The percentage reduction in the swelling in the treated and untreated paw as well as in both paws is calculated according to the equation $100 \cdot [1-(a-x)/(b-y)]$.

The following table shows the results of these tests for a few representative species of the compounds of this invention:

| Compound | Dose mg/kg p.o. | Percent Reduction Treated Paw 2nd day | Percent Reduction Treated Paw 14th day | Untreated paw 14th day |
|---|---|---|---|---|
| 2,6-bis-(diethylamino-acetylamino)-benzo[1,2-d:5,4-d']bisthiazole | 200 | 3 | 81 | 100 |
| 2,6-bis-(piperidino-acetylamino)-benzo[1,2-d:5,4-d']bisthiazole | 200 | 25 | 56 | 69 |
| 2,6-bis-(diethylamino-acetylamino)-4-chloro-8-trifluoromethyl-benzo[1,2-d:5,4-d']bisthiazole | 25 | 2 | 57 | 100 |
| 2,6-bis-(diethylamino-acetylamino)-4-chloro-8-nitrilo-benzo.[1,2-d:5,4-d']bisthiazole | 100 | 0 | 80 | 100 |
| 2,6-bis-(diethylamino-acetylamino)-4,8-dichloro-benzo[1,2-d:5,4-d']bisthiazole | 50 | 0 | 79 | 100 |
| 2,6-bis-(diethylamino-acetylamino)-4-bromo-benzo[1,2-d:5,4-d']bisthiazole | 50 | 0 | 52 | 97 |
| 2,6-bis-(diethylamino-acetylamino)-4-chloro-benzo[1,2-d:5,4-d']bisthiazole | 50 | 23 | 94 | 100 |
| 2,6-bis-(diethylamino-acetylamino)-4-bromo-8-chloro-benzo[1,2-d:5,4-d']bisthizaole | 50 | 5 | 68 | 100 |
| 2,6-bis-(o-methylpiperidino-acetylamino)-benzo[1,2-d:5,4-d']bisthiazole | 50 | 19 | 41 | 82 |
| 2,6-bis-(diethylamino-acetylamino)-4-methyl-benzo[1,2-d:5,4-d']-bisthiazole | 50 | 14 | 59 | 100 |
| 2,6-bis-(diethylamino-acetylamino)-benzo[1,2-d:5,4-d']-bisthiazole | 50 | 22 | 49 | 100 |
| 2,6-bis-(p-methyl-piperidino-acetylamino)-benzo[1,2-d:5,4-d']bisthiazole | 50 | 37 | 70 | 100 |
| 2,6-bis-(p-methyl-piperazino-acetylamino)-benzo[1,2-d:5,4-d']bisthiazole | 50 | 28 | 40 | 100 |
| 2,6-bis-(diethylamino-acetylamino)-4-bromo-benzo[1,2-d:5,4-d']bisthiazole | 50 | 12 | 80 | 100 |

The median lethal dose (LD50) of the compounds listed in the above table is far greater than 1000 mgm/kg p.o. Moreover, the compounds of this invention do not cause leukopenia.

For pharmaceutical purposes the compounds of the present invention are administered to warm-blooded animals peorally, parenterally, rectally or topically as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. The effective daily dosage range of the compounds according to the present invention is from 0.83 to 5.0 mgm/kg body weight, administered in 1 to 4 individual doses.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 28

Coated Pills

The pill core composition is compounded from the following ingredients:

| | |
|---|---|
| 2,6-Bis-(diethylamino-acetylamino)-benzo[1,2-d:5,4-d']bisthiazole | 100.0 parts |
| Lactose | 60.0 parts |
| Corn Starch | 35.0 parts |
| Gelatin | 3.0 parts |
| Magnesium stearate | 2.0 parts |
| Total | 200.0 parts |

Preparation

The active ingredient, the lactose and the corn starch are intimately admixed with each other, the mixture is moistened with an aqueous 10% solution of the gelatin, the moist mass is granulated through a 1 mm-mesh screen, and the granulate is dried at 40° C. and again passed through the screen. The dry granulate is admixed with the magnesium stearate, and the composition is compressed into 200 mgm pill core which are subsequently coated with a thin shell consisting essentially of a mixture of sugar, titanium dioxide, talcum and gum arabic, and polished with beeswax. Each coated pill is an oral dosage unit composition containing 100 mgm of the active ingredient.

EXAMPLE 29

Tablets

The tablet composition is compounded from the following ingredients:

| | |
|---|---|
| 2,6-Bis-(piperidino-acetylamino)-benzo[1,2-d:5,4-d']bisthiazole | 100.0 parts |
| Lactose | 70.0 parts |
| Corn Starch | 50.0 parts |
| Soluble Starch | 7.0 parts |
| Magnesium stearate | 3.0 parts |
| Total | 230.0 parts |

Preparation

The active ingredient and the magnesium stearate are intimately admixed with each other, the mixture is granulated with an aqueous solution of the soluble starch, and the granulate is dried. The dry granulate is admixed with the lactose and the corn starch, and the mixture is compressed into 230 mgm-tablets. Each tablet is an oral dosage unit composition containing 100 mgm of the active ingredient.

EXAMPLE 30

Ointment

The ointment composition is compounded from the following ingredients:

| | |
|---|---|
| 2,6-Bis-(diethylamino-acetylamino)-4-chloro-8-trifluoromethyl-benzo-[1,2-d:5,4-d']bisthiazole | 2.000 parts |
| Fuming hydrochloric acid | 0.011 parts |
| Sodium pyrosulfite | 0.050 parts |
| Mixture of equal parts of cetyl alcohol and stearyl alcohol | 20.000 parts |
| White vaseline | 5.000 parts |
| Synthetic bergamot oil | 0.075 parts |
| Distilled water q.s.ad | 100.000 parts |

Preparation

The ingredients are compounded in conventional manner into an ointment which is a topical composition containing 2 gm of the active ingredient per 100 gm of ointment.

EXAMPLE 31

Gelatin capsules

The capsule filler composition is compounded from the following ingredients:

| | |
|---|---|
| 2,6-Bis-(diethylamino-acetylamino)-4-chloro-8-cyano-benzo[1,2-d:-5,4-d']bisthiazole | 100.0 parts |
| Lactose | 250.0 parts |
| Corn Starch | 40.0 parts |
| Talcum | 10.0 parts |
| Total | 400.0 parts |

Preparation

The active ingredient, the lactose and the corn starch are intimately admixed with each other, the mixture is milled and then admixed with the talcum, and 400 mgm-portions of the composition are filled into hard gelatin capsules of suitable size. Each capsule is an oral dosage unit composition containing 100 mgm of the active ingredient.

EXAMPLE 32

Suppositories

The suppository composition is compounded from the following ingredients:

| | |
|---|---|
| 2,6-Bis-(diethylamino-acetylamino)-4-methyl-benzo[1,2-d:5,4-d']-bisthiazole | 0.1 parts |
| Cocoa Butter (M.P. 36–37° C.) | 1.6 parts |
| Carnauba wax | 0.1 parts |
| Total | 1.8 parts |

Preparation

The cocoa butter and the carnauba wax are melted and intimately admixed with each other, the mixture is cooled to 45° C., and the finely pulverized active ingredient is homogeneously blended into the mixture. 1.8 gm-portions of the compositions are poured into cooled suppository molds and allowed to harden therein. Each suppository is a rectal dosage unit composition containing 100 mgm of the active ingredient.

Any one of the other compounds embraced by formula I or a non-toxic, pharmacologically acceptable acid addition salt thereof may be substituted for the particular active ingredient in Examples 28 through 32. Likewise, the amount of active ingredient in these illustrative examples may be varied to achieve the dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula wherein
$R_1$ and $R_1'$ are each hydrogen or alkyl of 1 to 2 carbon atoms;
$R_2$ and $R_2'$ are each hydrogen or

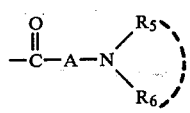

but other than both hydrogen at the same time, where

A is alkylene of 1 to 2 carbon atoms, $R_5$ is hydrogen, lower alkyl, lower alkyl-amino-lower alkyl, lower alkoxy-lower alkyl, hydroxycarbonyl-lower alkyl, cycloalkyl of 5 to 8 carbon atoms, lower alkyl-cycloalkyl of 5 to 8 carbon atoms, phenyl or morpholino;

$R_6$ is hydrogen, lower alkyl, lower alkyl-amino-lower alkyl or lower alkoxy-lower alkyl; or $R_5$ and $R_6$, together with each other and the nitrogen atom to which they are attached, form a piperidino or piperazino ring and said heterocyclic rings may optionally have one or two lower alkyl substituents, a lower alkoxy-carbonyl, a lower alkoxy-carbonyl-methyl, a hydroxy-lower alkyl, a trifluoroethyl, a cycloalkyl of 5 to 7 carbon atoms, a lower alkyl-cycloalkyl of 5 to 7 carbon atoms, a cyclohexylmethyl, a benzyl, a pyridyl, a piperidino, a phenyl, a fluoro-phenyl, a chloro-phenyl, a trifluoromethyl-phenyl, or an acetyl-phenyl substituent attached thereto; and $R_3$ and $R_4$ are each hydrogen, chlorine, bromine, lower alkyl, lower alkoxy, lower alkanoyl, hydroxy-carbonyl, lower alkoxy-carbonyl, aminocarbonyl, phenyl, trifluoromethyl, nitro, cyano or amino;

or a non-toxic, pharmacologically acceptable acid addition salt thereof.

2. A compound of claim 1, where $R_1$ and $R_1'$ are hydrogen, $R_2$ and $R_2'$ are both —CO—CH$_2$—NR$_5$R$_6$; where $R_5$ and $R_6$ are each hydrogen, methyl, ethyl or, together with each other and the nitrogen atom to which they are attached, piperidino or piperazino, where the heterocycles may optionally have a methyl, piperidino, phenyl or trifluoromethyl-phenyl substituent attached thereto; and $R_3$ and $R_4$ are each hydrogen, chlorine, bromine, methyl, methoxy, cyano or trifluoromethyl;

or a non-toxic, pharmacologically acceptable acid addition salt thereof.

3. A compound of claim 1, where $R_1$ and $R_1'$ are both hydrogen;

$R_2$ and $R_2'$ are both —CO—CH$_2$—NR$_5$R$_6$, where $R_5$ and $R_6$ are ethyl or, together with each other and the nitrogen atom to which they are attached, piperidino, methyl-piperidino, piperazino or methyl-piperazino;

$R_2$ is hydrogen, methyl-piperazino, chlorine or bromine; and $R_4$ is hydrogen, chlorine, bromine, cyano or trifluoromethyl;

or a non-toxic, pharmacologically acceptable acid addition salt thereof.

4. A compound of claim 1, which is 2,6-bis-(diethylamino-acetylamino)-benzo[1,2-d:5,4-d']bisthiazole or a nontoxic, pharmacologically acceptable acid addition salt thereof.

5. A compound of claim 1, which is 2,6-bis-(piperidino-acetylamino)-benzo[1,2-d:5,4-d']bisthiazole or a non-toxic, pharmacologically acceptable acid addition salt thereof.

6. A compound of claim 1, which is 2,6-bis-(diethylamino-acetylamino)-4-chloro-8-trifluoromethyl-benzo[1,2-d:5,4-d']bisthiazole or a non-toxic, pharmacologically acceptable acid addition salt thereof.

7. A compound of claim 1, which is 2,6-bis-(diethylamino-acetylamino)-4-chloro-8-cyanobenzo[1,2-d:5,4-d']bisthiazole or a nontoxic, pharmacologically acceptable acid addition salt thereof.

8. A compound of claim 1, which is 2,6-bis-(diethylamino-acetylamino)-4-methyl-benzo[1,2-d:5,4-d']bisthiazole or a non-toxic, pharmacologically acceptable acid addition salt thereof.

9. A compound of claim 1, which is 2,6-bis-(4-methyl-piperidino-acetylamino)-benzo[1,2-d:5,4-d']bisthiazole or a non-toxic, pharmacologically acceptable acid addition salt thereof.

10. A compound of claim 1, which is 2,6-bis-(diethylamino-acetylamino)-4,8-dichloro-benzo[1,2-d:5,4-d']bisthiazole or a non-toxic, pharmacologically acceptable acid addition salt thereof.

11. A compound of claim 1, which is 2,6-bis-(diethylamino-acetylamino)-4-bromo-benzo[1,2-d:5,4-d']bisthiazole or a non-toxic, pharmacologically acceptable acid addition salt thereof.

12. A compound of claim 1, which is 2,6-bis-(diethylamino-acetylamino)-4-chloro-benzo[1,2-d:5,4-d']bisthiazole or a non-toxic, pharmacologically acceptable acid addition salt thereof.

13. A compound of claim 1, which is 2,6-bis-(diethylamino-acetylamino)-4-bromo-8-chloro-benzo[1,2-d:5,4-d']bisthiazole or a non-toxic, pharmacologically acceptable acid addition salt thereof.

14. A compound of claim 1, which is 2,6-bis-(diethylamino-acetylamino)-4-chloro-8-bromo-benzo[1,2-d:5,4-d']bisthiazole or a non-toxic, pharmacologically acceptable acid addition salt thereof.

15. A compound of claim 1, which is 2,6-bis-(dimethylamino-acetylamino)-benzo[1,2-d:5,4-d']bisthiazole or a non-toxic, pharmacologically acceptable acid addition salt thereof.

16. A compound of claim 1, which is 2,6-bis-(o-methylpiperidino-acetylamino)-benzo[1,2-d:5,4-d']bisthiazole or a non-toxic, pharmacologically acceptable acid addition salt thereof.

17. A compound of claim 1, which is 2,6-bis-(p-methylpiperazino-acetylamino)-benzo[1,2-d:5,4-d']bisthiazole or a non-toxic, pharmacologically acceptable acid addition salt thereof.

18. A compound of claim 1, which is 2,6-bis-(ethylamino-acetylamino)-benzo[1,2-d:5,4-d]-bisthiazole or a non-toxic, pharmacologically acceptable acid addition salt thereof.

19. An antiarthritic or antirheumatic pharmaceutical dosage unit composition consisting essentially of an inert pharmaceutical carrier and an effective antiarthritic or antirheumatic amount of a compound of claim 1.

20. The method of relieving arthritis or rheumatism in a warm-blooded animal in need thereof, which comprises perorally, parenterally, rectally or topically administering to said animal an effective antiarthritic or antirheumatic amount of a compound of claim 1.

* * * * *

UNITED STATES PATENT AND TRADEMARK OFFICE
CERTIFICATE OF CORRECTION

PATENT NO. : 4,344,946                                   Page 1 of 2
DATED     : August 17, 1982
INVENTOR(S) : ERNEST CULLEN ET AL.

It is certified that error appears in the above—identified patent and that said Letters Patent is hereby corrected as shown below:

Title page, 5th line after second structural formula;
        Column 23, 5th line after structural formula;
        Column 1, line 40:
        "hydrox-" should be -- hydroxy- --.

Title page, 6th line after second structural formula;
        Column 23, 6th line after structural formula;
        Column 1, line 41:
        "ycarbonyl" should be -- carbonyl --.

Column 6, last line; Column 7, line 44:
        " <270°C" should be -- >270°C --.

Column 7, line 37: "thoery" should be -- theory --.

Column 8, lines 46 and 56; Column 12, line 35:
        "chloroa-" should be -- chloro- --.

Column 8, lines 47 and 57; Column 12, line 36:
        "cetyl" should be -- acetyl --.

Column 10, line 66; Column 11, line 3:
        "ethox-" should be -- ethoxy- --.

Column 10, line 67; Column 11, line 4:
        "ycarbonylbenzo" should be -- carbonyl-benzo --.

Column 11, line 42: "carbodii-" should be -- carbodi- --.

Column 11, line 43: "mide" should be -- imide --.

Column 14, line 28: ";" should be -- : --.

UNITED STATES PATENT AND TRADEMARK OFFICE
CERTIFICATE OF CORRECTION

PATENT NO. : 4,344,946
DATED : August 17, 1982
INVENTOR(S) : ERNEST CULLEN ET AL.

It is certified that error appears in the above—identified patent and that said Letters Patent is hereby corrected as shown below:

Column 14, line 48: "2,6-Bis-N-" should be -- 2,6-Bis-(N- --.

Column 14, line 66: "2,6-bis[N-ethoxycarbonylmethyl)" should be -- 2,6-bis[N-(ethoxycarbonylmethyl) --.

Column 15, line 8: "hydroxye-" should be -- hydroxy- --.

Column 15, line 9: "thyl" should be -- ethyl --.

Column 23, 4th line from bottom; Column 24, lines 5, 9, 13, 21, 25, 29, 33 and 37: "die-" should be -- di- --.

Column 23, 3rd line from bottom; Column 24, lines 6, 10, 14, 22, 26, 30, 34 and 38: "thylamino" should read -- ethylamino --.

Signed and Sealed this

Twenty-second Day of February 1983

[SEAL]

Attest:

GERALD J. MOSSINGHOFF

Attesting Officer     Commissioner of Patents and Trademarks